United States Patent [19]

Delannoy

[11] Patent Number: 4,911,155
[45] Date of Patent: Mar. 27, 1990

[54] MANUFACTURING PROCESS FOR A COHESIVE COMPRESSION BANDAGE, THE MEANS OF IMPLEMENTATION AND THE BANDAGE OBTAINED

[75] Inventor: Robert Delannoy, Paris, France
[73] Assignee: Molinier S.A., France
[21] Appl. No.: 269,244
[22] PCT Filed: Feb. 17, 1988
[86] PCT No.: PCT/FR88/00086
  § 371 Date: Oct. 5, 1988
  § 102(e) Date: Oct. 5, 1988
[87] PCT Pub. No.: WO88/06031
  PCT Pub. Date: Aug. 25, 1988

[30] Foreign Application Priority Data

Feb. 17, 1987 [FR] France ................................ 8703355

[51] Int. Cl.$^4$ ............................................. A61F 13/00
[52] U.S. Cl. .................................... 128/155; 128/156; 128/170
[58] Field of Search ....................... 128/155, 156, 170; 427/176, 280, 288; 26/18.5; 28/165; 156/83.84, 229

[56] References Cited

U.S. PATENT DOCUMENTS

| 1,533,272 | 4/1925 | Respess | 128/170 |
|---|---|---|---|
| 4,207,885 | 6/1980 | Hampton et al. | |
| 4,366,814 | 1/1983 | Riedel | 128/156 |
| 4,484,574 | 11/1984 | DeRusha et al. | 128/170 |
| 4,699,133 | 10/1987 | Schafer et al. | |
| 4,737,400 | 4/1988 | Edison et al. | |

Primary Examiner—Richard J. Apley
Assistant Examiner—N. Paul
Attorney, Agent, or Firm—Steele, Gould & Fried

[57] ABSTRACT

Woven or knitted bandage material is pre-shrunk and wound on a roll. The material is fed from the roll via a positive roller drive that stretches the material to correspond to its initial stretch capacity. The fed material is continuously processed through shrinking, spray application of a watery emulsion of rubber, and drying, first on one side and then the other side. A plurality of inter-engageable rubber loops are obtained on the surface of the bandage material, which render the bandage cohesive.

14 Claims, 2 Drawing Sheets

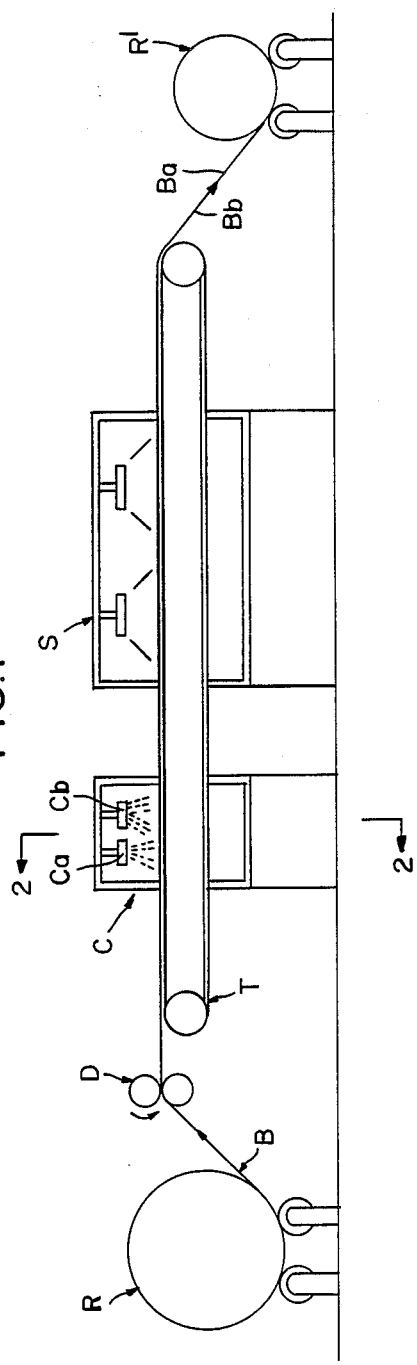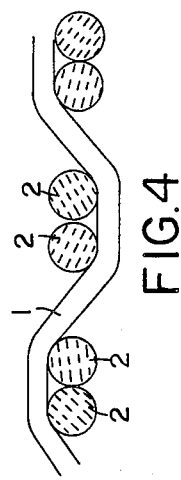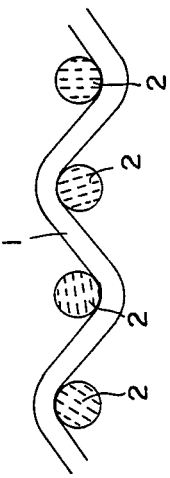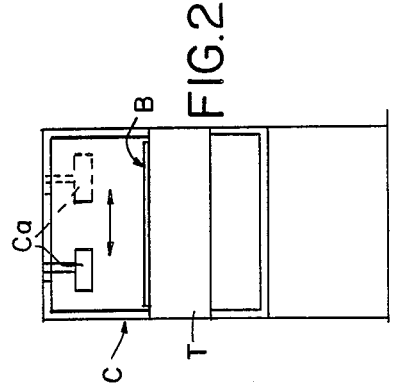

MANUFACTURING PROCESS FOR A COHESIVE COMPRESSION BANDAGE, THE MEANS OF IMPLEMENTATION AND THE BANDAGE OBTAINED

BACKGROUND OF THE INVENTION

1. Field of the Invention

The invention relates to a manufacturing process for a cohesive compression bandage, the means of implementation and the bandage obtained.

The object of the invention is related to the technical sector for bandages.

2. Prior Art

Cohesive compression bandages are already known, i.e. bandages likely to stick to themselves and not to the skin. With these types of bandages, it is necessary to distinguish those which are obtained on a non-woven support and those which are obtained on a woven or knitted support. In general, the cohesive feature is due to a fine spray of droplets of latex.

SUMMARY OF THE INVENTION

This invention relates to the woven or knitted type compression bandages and is aimed at a particular implementation process which gives the bandage compression and cohesion qualities making it particularly well adapted in the field of phlebology and sports traumas.

The cohesive bandage obtained has a stretch capacity between 70 and 90% with a crimped and airy finish.

In order to achieve the goal, during the manufacturing process:

the bandage material is subjected to a shrinking operation in order to give a stretch capacity between 110 and 140%, the bandage material is wound into an initial roll.

the roll is controlled by a drive component to provide positive unrolling corresponding to the initial stretch capacity between 110 and 140%, then in a successive and continuous manner, on outlet from the roll, the bandage material is subjected to a shrinking operation to provide it with a stretch capacity between 90 and 110%, oneof the faces of the bandage material is subjected to a watery natural rubber emulsion, this face is subjected to a drying operation, the bandage material is wound on to a take up roll so that the emulsioned face is on the inside, the take up roll is moved to replace the initial roll, the other face of the bandage material is successively subjected to a watery emulsion of natural rubber and, when dry a plurality of rubber loops results which are likely to be entangled when two parts of the bandage are put into contact and under pressure.

Other features will appear as the specification proceeds.

BRIEF DESCRIPTION OF THE DRAWINGS

The invention is described below in more detail with the help of the drawings which represent only an exemplary embodiment:

FIG. 1 is a purely schematic view illustrating the unit to implement the process, FIG. 2 is a cross transversal sectional view taken on the line 2.2 of FIG. 1, FIGS. 3 and 4 are large scale partial longitudinal sectional views of the bandage material.

DETAILED DESCRIPTION OF THE PREFERRED EMBODIMENTS

Figure 5:
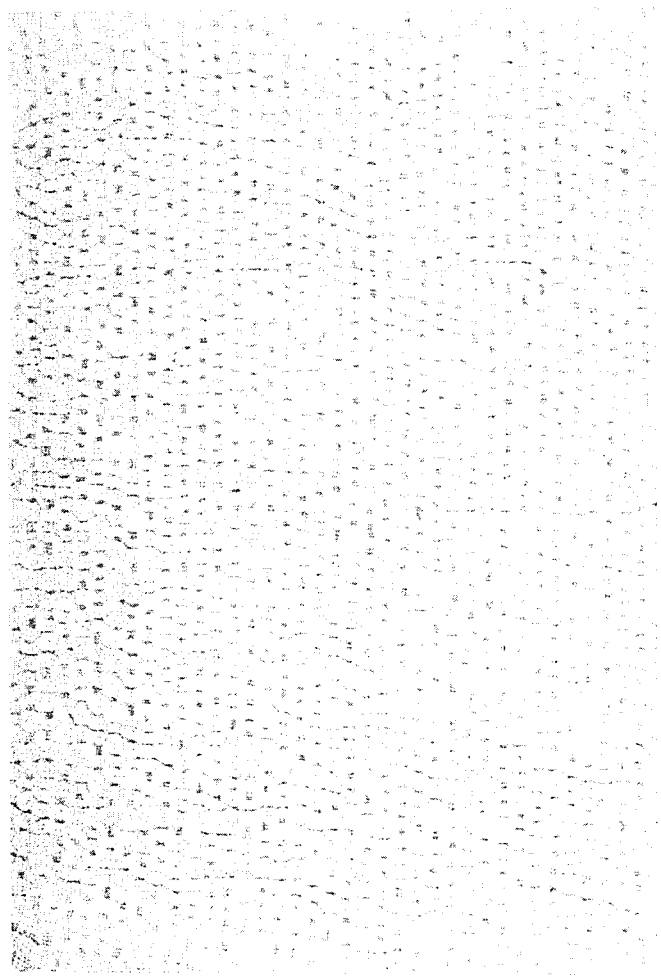
FIG. 5 shows a sample of an example of embodiment of the cohesive bandage.

The object of the invention will become more apparent from the following non limiting detailed description when considered in conjunction with the accompanying drawings.

The bandage is obtained from a fabric resulting from weaving warp threads (1) and filling threads (2) according to a weaving pattern. This weaving can be conventional, i.e. successive weaving of a warp thread and filling thread (FIG. 3) or the weaving can be carried out on a crocheting machine by successive weaving of a warp thread (1) and two filling threads (2) (FIG. 4).

Several modes of weaving and knitting can be provided depending on the type of threads, e.g.:

warp composed of extensible threads and non extensible filling threads, warp and filling composed of extensible threads, warp alternately composed of extensible or non-extensible threads, filling of extensible threads.

By way of a non-restrictive example, the threads comprising the fabric are of cotton, viscose and elasthane in the following proportions:

cotton: 21% viscose: 78.2% elastane: 0.8%

FIG. 1 illustrates an example of equipment for implementing the process. After weaving or knitting, the bandage material (B) is subjected to prior steam shrinking which gives it a stretch capacity between 110 and 140%. The bandage material is then wound into a roll.

The roll (R) of bandage material is controlled by a drive component designed to positively unroll the bandage material corresponding to the initial stretch capacity between 110and 140%. On the outlet of the roll (R), the bandage material (B) is subjected to a drive roll (D) to give it a stretch capacity to within 90 and 110%. The bandage material is then transferred by means of a belt conveyor (T), to a spray chamber (C) for application of a watery emulsion of natural liquid latex type rubber or another rubber adhesive liquid material. On leaving the spray chamber, the emulsioned face (Ba) passes through a drying chamber (S) and is then wound on to a take up roll (R1) so that the emulsioned face is on the inside.

The take up roll (R1) is then positioned on a roll mandrel controlled by a positive roller (D) so as to transfer, in the aforementioned conditions, the bandage material (B) to the spray chamber in order to subject the other face (Bb) to a latex spray and then a drying operation. Therefore, a plurality of latex loops are obtained and are likely to be entangled when two parts of the resulting bandage are put into contact and under pressure. The bandage is thereby provided with the desired cohesive feature.

It is to be noted that the spray chamber implements means which are well known and designed to provide constant and even distribution of the watery emulsion of natural rubber on each face of the bandage material.

This spraying operation is preferably carried out by means of two close joining nozzles (Ca) and (Cb). Similarly, considering that the band of bandage material, obviously for reasons of economy, is processed in widths larger than the size of standard bandages, the nozzles are fixed to a support so as to be moved sideways and alternately, oscillating transverse to a feed direction of the bandage material to thereby cover the full width of the bandage material as when it is moved.

On leaving the unit, after the various treatments and stages, a cohesive bandage material is obtained, with a stretch capacity between 70 and 90%. The selvedges are compressed to enable the bandage material to be torn crosswise manually without using any kind of cutting tool.

Furthermore, the impregnation thus obtained by spraying with a watery emulsion of natural rubber, facilitates the manual tearing of the loop. Obviously, the width of the bandage is material divided into different widths corresponding to the widths of standardized bandages.

Similarly, in order to provide a better gripping effect of the latex on the bandage, all the filling threads can be cotton.

FIG. 5 refers to drawings which show a sample of the cohesive bandage according to the invention. Obviously this bandage's finish can be different and have a more or less airy effect as a function of the basic weave or knit pattern used.

The cohesive compression bandage resulting from the process, maintains its therapeutic qualities and is particularly recommended in the field of phlebology and sports traumas.

I claim:

1. A process for preparing a cohesive compression bandage from a bandage material obtained by weaving or knitting, comprising the steps of:
   shrinking the bandage material to obtain an initial stretch capacity between 110 and 140%;
   winding the bandage material into a roll;
   positively feeding the bandage material from said roll to correspond with the initial stretch capacity between 110 and 140%, then in a successive and continuous manner:
      shrinking the bandage material fed from the roll to give the bandage material a stretch capacity between 90 and 110%,
      spraying a face of the bandage material with a spray of a watery emulsion of natural rubber,
      drying said face of the bandage material,
      spraying an other face of the bandage material with a watery emulsion of natural rubber and then drying the resulting bandage;
   whereby a plurality of rubber loops are obtained in the bandage material, the rubber loops being likely to be entangled when two parts of the bandage are put into contact and under pressure.

2. The process according to claim 1, wherein the bandage is woven or knitted in a width larger than a spray pattern of a nozzle and the watery emulsion of natural rubber is sprayed through the nozzle while moving the nozzle to cover a full width of the said bandage material.

3. The process according to claim 1, further comprising compressing the bandage material to form selvedges, whereby the bandage material readily can be torn.

4. An apparatus for preparing a cohesive compression bandage from bandage material, comprising:
   means for feeding the bandage material at a stretch capacity between 110 and 140%;
   a positively driven roll operable to give the fed bandage material a stretch capacity between 90 and 100%;
   a spray chamber fitted with at least one nozzle for spraying onto the bandage material a watery emulsion of natural rubber, the nozzle being movable to cover a full width of the bandage material; and,
   a drying chamber for drying said bandage material.

5. A bandage prepared according to claim 2, wherein the bandage has a stretch capacity between 70 and 90%.

6. The bandage according to claim 5, wherein the bandage has a warp composed of extensible threads, and a filling composed of non-extensible threads.

7. The bandage according to claim 5, wherein the bandage has a warp composed of extensible threads and non-extensible threads, and a filling composed of non-extensible threads.

8. The bandage according to claim 5, wherein the bandage has a warp composed of extensible threads, and a filling composed of extensible threads.

9. The bandage according to claim 5, wherein the bandage has a warp composed of extensible threads and non-extensible threads, and a filling composed of extensible threads.

10. The bandage according to claim 5, wherein the bandage material is woven.

11. The bandage according to claim 5, wherein the bandage material is knitted.

12. A bandage prepared according to the process of claim 1.

13. The process according to claim 1, comprising, after said one face of the bandage material is dried, winding said bandage material onto a take up roll so that said one face having the rubber thereon is on an inside, then placing the take up roll in place of the initial roll, and repeating the spraying and drying steps on said other side of the bandage material.

14. The process according to claim 2, wherein said spraying step is accomplished by oscillating the nozzle transversely to a feed direction of the bandage material to thereby cover said full width of the bandage material.

* * * * *